(12) United States Patent
Geiger et al.

(10) Patent No.: US 12,076,158 B2
(45) Date of Patent: Sep. 3, 2024

(54) INTUITIVE DISPLAY FOR ROTATOR CUFF TEAR DIAGNOSTICS

(71) Applicants: SIEMENS HEALTHINEERS AG, Forchheim (DE); New York University, New York, NY (US)

(72) Inventors: Bernhard Geiger, Cranbury, NJ (US); Michael Schwier, Hamburg (DE); Sasa Grbic, Plainsboro, NJ (US); Esther Raithel, Dormitz (DE); Dana Lin, New York, NY (US); Guillaume Chabin, Paris (FR)

(73) Assignees: Siemens Healthineers AG, Forchheim (DE); New York University, New York, NY (US)

( * ) Notice: Subject to any disclaimer, the term of this patent is extended or adjusted under 35 U.S.C. 154(b) by 240 days.

(21) Appl. No.: 17/168,213

(22) Filed: Feb. 5, 2021

(65) Prior Publication Data
US 2022/0249014 A1    Aug. 11, 2022

(51) Int. Cl.
*A61B 5/00* (2006.01)
*G06T 7/10* (2017.01)
(Continued)

(52) U.S. Cl.
CPC .......... *A61B 5/4576* (2013.01); *A61B 5/4519* (2013.01); *A61B 5/4523* (2013.01);
(Continued)

(58) Field of Classification Search
CPC ..... A61B 5/055; A61B 5/4519; A61B 5/4523; A61B 5/4576; A61B 5/7267; A61B 5/742; A61B 5/7475; A61B 8/08; A61B 6/032; G06T 7/10; G06T 7/30; G06T 2207/10081; G06T 2207/10088; G06T 2207/10132; G06T 2207/20081; G06T 2207/30004;
(Continued)

(56) References Cited

U.S. PATENT DOCUMENTS 7,627,159 B2    12/2009    Kiraly et al.
9,542,741 B2    1/2017    Birkbeck et al.
(Continued)

FOREIGN PATENT DOCUMENTS

EP    2554120 A1    2/2013
EP    3537447 A1    9/2019
(Continued)

OTHER PUBLICATIONS

Extended European Search Report (EESR) mailed Jul. 4, 2022 in corresponding European Patent Application No. 22154873.8.
(Continued)

*Primary Examiner* — Pascal M Bui Pho
*Assistant Examiner* — Neshat Baset (57) ABSTRACT

Systems and methods for an intuitive display of one or more anatomical objects are provided. One or more 3D medical images of one or more anatomical objects of a patient are received. Correspondences between the one or more 3D medical images and points on a 2D map representing the one or more anatomical objects are determined. The 2D map is updated with patient information extracted from the one or more 3D medical images. The updated 2D map with the determined correspondences is output.

11 Claims, 3 Drawing Sheets

(51) Int. Cl.
| | |
|---|---|
| *G06T 7/30* | (2017.01) |
| *A61B 5/055* | (2006.01) |
| *A61B 6/03* | (2006.01) |
| *A61B 8/08* | (2006.01) |

(52) U.S. Cl.
CPC ............ *A61B 5/7267* (2013.01); *A61B 5/742* (2013.01); *A61B 5/7475* (2013.01); *G06T 7/10* (2017.01); *G06T 7/30* (2017.01); *A61B 5/055* (2013.01); *A61B 6/032* (2013.01); *A61B 8/08* (2013.01); *G06T 2207/10081* (2013.01); *G06T 2207/10088* (2013.01); *G06T 2207/10132* (2013.01); *G06T 2207/20081* (2013.01); *G06T 2207/30004* (2013.01)

(58) Field of Classification Search
CPC . G06T 2207/20084; G06T 2207/20101; G06T 2207/20112; G06T 7/0014; G06T 7/33; G06T 7/11; G16H 50/20; G16H 50/70; G16H 30/40; G16H 30/20; G06N 3/04; G06N 3/08; G01R 33/48; G01R 33/4808; G01R 33/4812; G01R 33/54
See application file for complete search history.

(56) References Cited

U.S. PATENT DOCUMENTS

| | | | |
|---|---|---|---|
| 9,558,568 B2 | 1/2017 | Kretschmer et al. | |
| 11,259,874 B1* | 3/2022 | Landon | G16H 40/67 |
| 11,468,567 B2* | 10/2022 | Groth | A61B 5/7475 |
| 2011/0311116 A1* | 12/2011 | Benn | G06T 11/00 382/128 |
| 2014/0152649 A1* | 6/2014 | Moeller | G06T 19/00 345/419 |
| 2016/0328855 A1* | 11/2016 | Lay | G06K 9/6282 |
| 2017/0231713 A1 | 8/2017 | Siewerdsen et al. | |
| 2017/0323443 A1* | 11/2017 | Dhruwdas | G06T 11/006 |
| 2018/0293727 A1 | 10/2018 | Fenchel et al. | |
| 2020/0167911 A1 | 5/2020 | Park et al. | |
| 2021/0012884 A1* | 1/2021 | Kim | G06K 9/6268 |
| 2022/0039868 A1* | 2/2022 | Chaoui | A61B 5/743 |

FOREIGN PATENT DOCUMENTS

| | | |
|---|---|---|
| EP | 3389006 B1 | 2/2020 |
| EP | 3657433 A1 | 5/2020 |
| WO | WO2006056923 A1 | 6/2006 |

OTHER PUBLICATIONS

Galbusera Fabio et al: "Artificial intelligence and machine learning in spine research", JOR Spine, vol. 2, No. 1, Mar. 22, 2019 (Mar. 22, 2019), p. e1044, Retrieved from the Internet: URL:https://onlinelibrary.wiley.com/doi/full-XML/10.1002/jsp2.1044.

Wolf I et al: "The Medical Imaging Interaction Toolkit", Medical Image Analysis, Oxford University Press, Oxofrd, GB, vol. 9, No. 6, Dec. 1, 2005 (Dec. 1, 2005), pp. 594-604, [retrieved on Dec. 1, 2005].

Shim Eungjune et al: "Automated rotator cuff tear classification using 3D convolutional neural network", Scientific Reports, vol. 10, No. 1, Dec. 1, 2020 (Dec. 1, 2020), Retrieved from the Internet: URL:https://www.nature.com/articles/s41598-020-72357-0.pdf.

Taghizadeh Elham et al: "Deep learning for the rapid automatic quantification and characterization of rotator cuff muscle degeneration from shoulder CT datasets", European Radiology, vol. 31, No. 1 , pp. 181-190.

Athwal et al., "Rotator Cuff Tears," 2017, retrieved online from https://orthoinfo.aaos.org/en/diseases-conditions/rotator-cuff-tears, 8 pgs.

Okoroha et al., "Characterization of Rotator Cuff Tears: Ultrasound Versus Magnetic Resonance Imaging," 2017, Orthopedics, vol. 40, No. 1, pp. e124-e130.

Morag et al., "MR Imaging of Rotator Cuff Injury: What the Clinician Needs to Know," 2016, RadioGraphics, vol. 26, No. 4, pp. 1045-1065.

"MR Procedure Volume and Mix by Type of Procedure." IMV 2016 MR Market Outlook Report.

Sambandam et al., "Rotator Cuff Tears: An Evidence Based Approach," 2015, World Journal of Orthopedics, vol. 6., No. 11, pp. 902-918.

Paloneva et al., "Increasing Incidence of Rotator Cuff Repairs—A Nationwide Registry Study in Finland," 2015, BMC Musculoskeletal Disorders, vol. 16, No. 189, pp. 1-6.

Ensor et al., "The Rising Incidence of Rotator Cuff Repairs," 2013, Journal of Shoulder and Elbow Surgery, vol. 22, Issue 12, pp. 1628-1632.

Spencer Jr. et al., "Interobserver Agreement in the Classification of Rotator Cuff Tears Using Magnetic Resonance Imaging," 2008, The American Journal of Sports Medicine, vol. 36, No. 1, pp. 99-103.

\* cited by examiner

INTUITIVE DISPLAY FOR ROTATOR CUFF TEAR DIAGNOSTICS

TECHNICAL FIELD

The present invention relates generally to an intuitive display system and method, and in particular to an intuitive display for rotator cuff tear diagnostics.

BACKGROUND

The rotator cuff is a group of muscles and tendons that surround the shoulder joint, keeping the head of the humerus in the socket of the shoulder. Rotator cuff tears are one of the most common causes of shoulder pain. In the current clinical practice, MRI (magnetic resonance imaging) is considered the standard of care for rotator cuff assessment and treatment planning. Currently, interpretation of MRI images is manually performed by radiologists by scrolling through a large number of MRI images to detect rotator cuff tears and measuring or estimating the size of the detected rotator cuff tears. However, such manual interpretation of MRI imaging can be complex and time consuming, requiring analysis of several image series acquired in different imaging planes. For example, measurement of rotator cuff tears is performed in two dimensions on different imaging planes. Recently, artificial intelligence based methods have been proposed for automatically diagnosing and measuring rotator cuff tears. While such artificial intelligence based methods may increase the speed of the interpretation of MRI imaging, the findings of the artificial intelligence based methods need to be manually verified by a user.

BRIEF SUMMARY OF THE INVENTION

In accordance with one or more embodiments, systems and methods for an intuitive display of one or more anatomical objects are provided. One or more 3D medical images of one or more anatomical objects of a patient are received. Correspondences between the one or more 3D medical images and points on a 2D map representing the one or more anatomical objects are determined. The updated 2D map with the determined correspondences is output.

In one embodiment, the correspondences are determined between 2D slices of the one or more 3D medical images and the points on the 2D map. In another embodiment, the correspondences are determined between locations in the one or more 3D medical images and the points on the 2D map. In one embodiment, user input selecting one of the points on the 2D map is received and, in response to receiving the user input, one or more of the 2D slices of the one or more 3D medical images that correspond to the selected point are displayed based on the determined correspondences.

In one embodiment, the correspondences between the one or more 3D medical images and the points on the 2D map are determined based on user input. In another embodiment, the correspondences between the one or more 3D medical images and the points on the 2D map are determined by automatically identifying landmarks in the one or more 3D medical images using a trained machine learning based network and associating the automatically identified landmarks to points on the 2D map. In another embodiment, the correspondences between the one or more 3D medical images and the points on the 2D map are determined by creating an atlas of the one or more anatomical objects, annotating the atlas with anatomical features that correspond to anatomical feature in the 2D map, and registering the annotated atlas with the one or more 3D medical images. In another embodiment, the correspondences between the one or more 3D medical images and the points on the 2D map are determined by creating an atlas of the one or more anatomical objects, annotating the atlas with anatomical features that correspond to anatomical feature in the 2D map, segmenting one or more anatomical structures from the one or more 3D medical images and from the annotated atlas, and registering the annotated atlas with the one or more 3D medical images based on the one or more anatomical structures segmented from the one or more 3D medical images and the one or more anatomical structures segmented from the annotated atlas.

In one embodiment, the one or more anatomical objects is associated with a rotator cuff of the patient. The 2D map may represent one or more muscles of the rotator cuff in an unfolded state. In one embodiment, a muscle quality of one or more muscles of the rotator cuff is automatically determined from the one or more 3D medical images using a trained machine learning based network and the one or more muscles are represented in the 2D map based on the automatically determined muscle quality. In one embodiment, a location and a size of a tear in a muscle of the rotator cuff are automatically determined from the one or more 3D medical images using a trained machine learning based network and the tear in the muscle is represented in the 2D map based on the automatically determined location and size of the tear. The 2D map may also comprise text labels identifying structures of the one or more anatomical objects.

These and other advantages of the invention will be apparent to those of ordinary skill in the art by reference to the following detailed description and the accompanying drawings.

DETAILED DESCRIPTION

The present invention generally relates to an intuitive display for rotator cuff tear diagnostics. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for an intuitive display for rotator cuff tear diagnostics by generating a 2D (two dimensional) map representing the rotator cuff of a patient. Correspondences between points on the 2D map and one or more 3D (three dimensional) images of the patient are determined, thereby allowing a user (e.g., a radiologist or a clinician) to interact with the 2D map to view the relevant 2D slices. The 2D map also shows various information of interest, such as, e.g., anatomical labels, tears in the muscles of the rotator cuff, and muscle quality of the muscles of the rotator cuff, which may be automatically determined using machine learning based networks. Advantageously, the 2D map representing the rotator cuff in accordance with embodiments described herein significantly reduces the time for the user to verify the automatically determined findings of the machine learning based networks. Additionally, the 2D map efficiently presents findings to the user and provides information of interest that may reduce errors in diagnostics.

Figure 1:
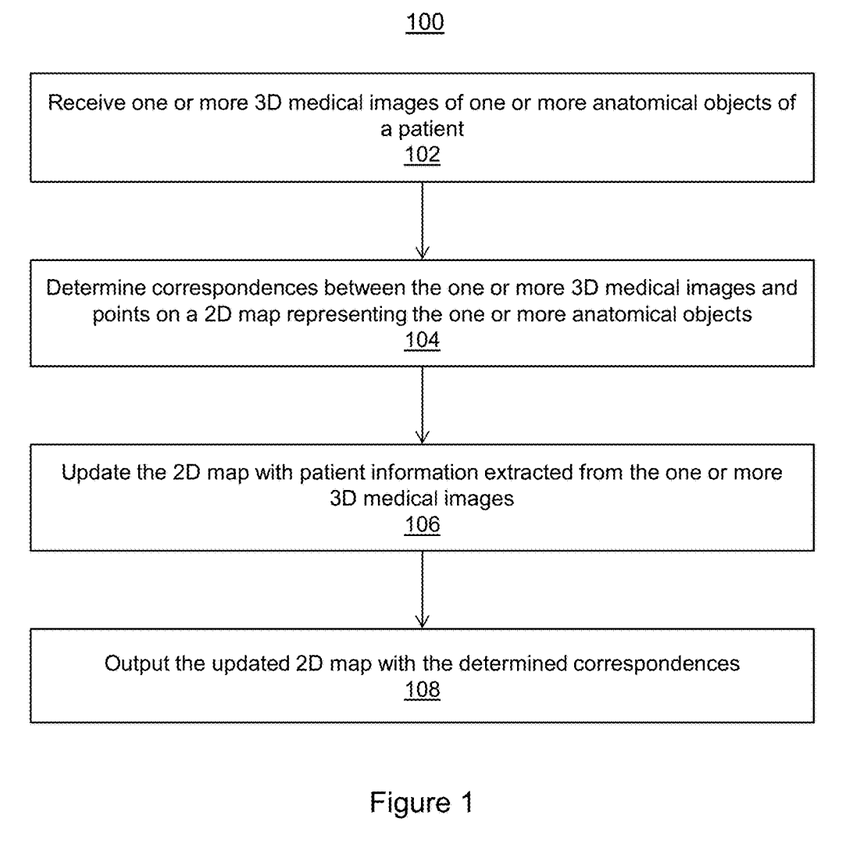
FIG. 1 shows a method for generating a 2D map representing one or more anatomical objects, in accordance with one or more embodiments.

FIG. 1 shows a method 100 for generating a 2D map representing one or more anatomical objects, in accordance with one or more embodiments. The steps of method 100 may be performed by one or more suitable computing devices, such as, e.g., computer 302 of FIG. 3.

At step 102, one or more 3D medical images of one or more anatomical objects of a patient are received. In one embodiment, the one or more anatomical objects comprise anatomical objects of interest associated with the rotator cuff of the patient, such as, e.g., muscles and tendons (e.g., the supraspinatus, infraspinatus, teres minor, and subscapularis muscles) associated with the rotator cuff, bones (e.g., the humerus and scapula) coupled to such muscles and tendons, and any other anatomical objects of interest associated with the rotator cuff. However, it should be understood that the one or more anatomical objects may comprise other organs, bones, vessels, or any other suitable anatomical structures of the patient.

The 3D medical images may comprise a plurality of 3D medical images acquired with different acquisition parameters and/or different imaging planes. Each of the 3D medical images comprises a plurality of 2D slices depicting a cross section of the 3D medical image. In one embodiment, the 3D medical images include MRI (magnetic resonance imaging) images. However, the input image may be of any other suitable modality, such as, e.g., CT (computed tomography), US (ultrasound), or any other modality or combination of modalities. The 3D medical images may be received directly from an image acquisition device (e.g., image acquisition device 314 of FIG. 3), such as, e.g., an MRI scanner, as the images are acquired, or can be received by loading previously acquired images from a storage or memory of a computer system or receiving the images from a remote computer system.

At step 104, correspondences between the one or more 3D medical images and points on a 2D map representing the one or more anatomical objects are determined. The 2D map may be a symbolic representation of the anatomical objects to facilitate user understanding. For example, where the anatomical objects are anatomical objects of interest associated with the rotator cuff of the patient, the 2D map may comprise a 2D representation of the supraspinatus muscle, infraspinatus muscle, teres minor muscle, and subscapularis muscle of the rotator cuff coupled between the humerus bone and the scapula bone. In one embodiment, the supraspinatus muscle, infraspinatus muscle, teres minor muscle, and subscapularis muscle are depicted in the 2D map in a 2D unfolded state, unfolded based on the 3D medical images using any suitable (e.g., known) technique.

The correspondences associate the 3D medical images with one or more points on the 2D map. In one example, the correspondences associate one or more 2D slices of the 3D medical images with corresponding points in the 2D map. In another example, the correspondences associate locations in the 3D medical images (i.e., locations in the 2D slices) with a corresponding location in the 2D map. The points on the 2D map may be any suitable point.

In one embodiment, the correspondences between the one or more 3D medical images and points on the 2D map are determined based on user input. For example, a user may select a point on the 2D map, navigate to one or more 2D slices that depict the corresponding location of the selected point, and select the one or more 2D slices or corresponding location of the selected point on the one or more 2D slices.

In another embodiment, the correspondences between the one or more 3D medical images and points on the 2D map are automatically determined using a trained machine learning based network. For example, the trained machine learning based network may be trained (during a prior offline or training stage) with annotated training data to automatically identify anatomically significant landmarks in the 3D medical images. The anatomically significant landmarks may be, e.g., insertion points where muscles of the rotator cuff attach to the humerus bone and the scapula bone. The automatically identified landmarks in the 3D medical images are associated with 2D points on the 2D map. Other points in the 2D map are associated with locations in the 3D medical images by linear interpolation. In particular, for a given point in the 2D map, a triangle may be formed by its three nearest neighbors and interpolation weights can be the barycentric coordinates in the 3D medical images.

In another embodiment, the correspondences between the one or more 3D medical images and points on the 2D map are determined by creating an atlas of the one or more anatomical objects (e.g., by averaging a 3D dataset). The atlas is then annotated with anatomical features that correspond to anatomical features in the 2D map. The annotated atlas is then registered (e.g., a 3D affine or deformable registration) with the 3D medical images of the patient to thereby establish correspondences between the 2D map and the 3D medical images.

In another embodiment, the correspondences between the one or more 3D medical images and points on the 2D map are determined by creating an atlas of the one or more anatomical objects (e.g., by averaging a 3D dataset) and annotating the atlas with anatomical features that correspond to anatomical features in the 2D map, as described above. Anatomical structures are then segmented from the 3D medical images and the annotated atlas. For example, the supraspinatus, infraspinatus, teres minor, and subscapularis muscles may be segmented from the 3D medical images and the annotated atlas using a trained machine learning based network. The annotated atlas is then registered with the 3D medical images of the patient based on the segmented anatomical structures to establish correspondences between the 2D map and the 3D medical images.

In one embodiment, initial correspondences may be determined (e.g., according to embodiments described herein, such as based on user input, using an artificial intelligence system to automatically identify anatomically significant landmarks, by registering an annotated atlas with the 3D medical images (e.g., 3D affine or deformable registration or registration based on segmentation), as discussed above) and the initial correspondences may be iteratively refined based on user input to determine the correspondences between the one or more 3D medical images and points on the 2D map. For example, the initial correspondences may be iteratively refined by a user for any number of iterations to adjust the corresponding locations either on the 2D map or on the 2D slices of the 3D medical images.

At step 106, the 2D map is updated with patient information extracted from the one or more 3D medical images.

The patient information may comprise anatomical landmarks identified in the one or more 3D medical images, a muscle quality (e.g., a Goutallier score) determined from the one or more 3D medical images, muscle tears determined from the one or more 3D medical images, or any other information of interest of the patient determined from the one or more 3D medical images. Such patient information facilitates interpretation of the 2D map for a user.

Figure 2:
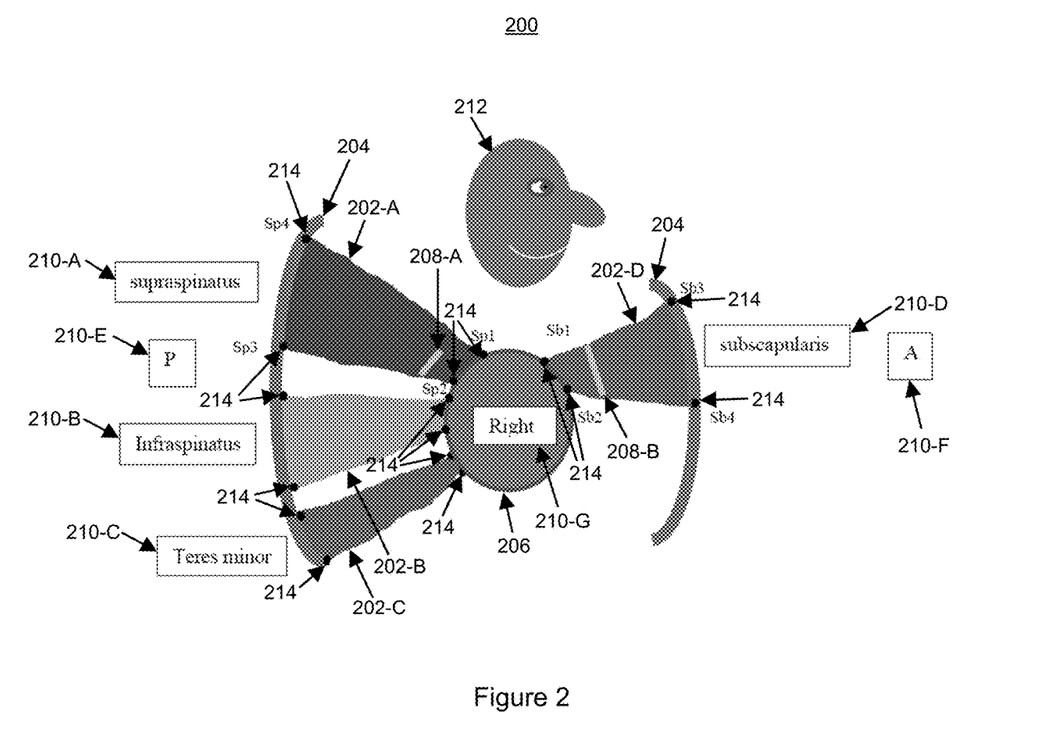
FIG. 2 shows an exemplary 2D map of the rotator cuff of a patient, in accordance with one or more embodiments.

FIG. 2 shows an exemplary 2D map 200 of the rotator cuff of a patient updated with patient information extracted from 3D medical images, in accordance with one or more embodiments. As shown in FIG. 2, 2D map 200 comprises a 2D representation of supraspinatus muscle 202-A, infraspinatus muscle 202-B, teres minor muscle 202-C, and subscapularis muscle 202-D (collectively referred to as muscles 202) of the rotator cuff in an unfolded state coupled between humerus bone 206 and scapula bone 204. 2D map 200 depicts various patient information associated with the rotator cuff of the patient extracted from 3D medical images.

In one embodiment, the various patient information may be depicted by text labels 210-A, 210-B, 210-C, and 210-D respectively identifying supraspinatus muscle 202-A, infraspinatus muscle 202-B, teres minor muscle 202-C, and subscapularis muscle 202-D (or any other relevant anatomical landmarks or structures). The various patient information may also be depicted by text labels 210-E and 210-F respectively identifying posterior and anterior anatomical locations (or any other relevant anatomical locations). The various patient information may further be depicted by text label 210-G identifying that the rotator cuff is of the right shoulder of the patient. In one embodiment, the various patient information may be depicted by an avatar 212 identifying an orientation of the patient.

In one embodiment, the various patient information depicted in 2D map 200 comprises patient information automatically determined using artificial intelligence or machine learning based networks. In one example, a trained machine learning based network may be utilized to automatically determine a muscle quality of muscles 202, such as, e.g., a Goutallier score. Muscles 202 may be represented in 2D map 200 based on the muscle quality. For example, muscles 202 may be color coded in 2D map 200 based on the automatically determined muscle quality or may be represented in 2D map 200 with a pattern corresponding to the automatically determined muscle quality. In another example, a trained machine learning based network may be utilized to automatically determine a location and size of tears 208-A and 208-B in muscles 202. The automatically determined location of tears 208-A and 208-B are represented as straight lines in 2D map 200 at the approximate location of the tear in muscles 202. As shown in FIG. 2, tear 208-A is shown as a partial tear that does not extend through supraspinatus muscle 202-A while tear 208-B is shown as a full tear that extends through subscapularis muscle 202-D. The automatically determined size (e.g., small, medium, large, or massive) of tears 208-A and 208-B are represented on 2D map 200 by, e.g., color coding tears 208-A and 208-B based on the automatically determined tear size, representing tears 208-A and 208-B with a pattern corresponding to the automatically determined tear size, etc. Other patient information automatically determined using trained machine learning based networks may also be represented in 2D maps. The trained machine learning based networks utilized herein may be any suitable machine learning based network (e.g., neural networks, support vector machines, decision trees, Bayesian networks, etc.) implemented according to any suitable (e.g., known) technique. The trained machine learning based networks are trained during a prior offline or training stage and, once trained, applied to automatically determine the various patient information during an online or testing stage.

2D map 200 comprises a number of points 214 of interest. In FIG. 2, points 214 of interest are insertion points where muscles 202 attach to humerus bone 206 and/or scapula bone 204. However, points 214 of interest may be any other points of interest, such as, e.g., user selected points, anatomically significant points, etc. The points 214 of interest may be the points on the 2D map at which correspondences between the one or more 3D medical images are determined at step 104 of FIG. 1.

At step 108, the updated 2D map with the determined correspondences are output. For example, the updated 2D map with the determined correspondences can be output by displaying the updated 2D map with the determined correspondences on a display device of a computer system, storing the updated 2D map with the determined correspondences on a memory or storage of a computer system, or by transmitting the updated 2D map with the determined correspondences to a remote computer system.

In one embodiment, the updated 2D map with the determined correspondences is presented to a user to, e.g., assess a rotator cuff tear or to verify automatically determined findings (e.g., location of tears, size of tears, muscle quality, etc.) of a trained machine learning based network. The user may interact with the updated 2D map by selecting points on the 2D map. In one example, user input selecting the points on the 2D map is received and, in response to receiving the user input, one or more 2D slices of the 3D medical images that correspond to the selected points in accordance with the determined correspondences are presented to the user. In another example, user input selecting the points on the 2D map is received and, in response to receiving the user input, locations in the one or more 3D medical images (e.g., locations identified in 2D slices of the one or more 3D medical images) that correspond to the selected points in accordance with the determined correspondences are presented to the user.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 3:
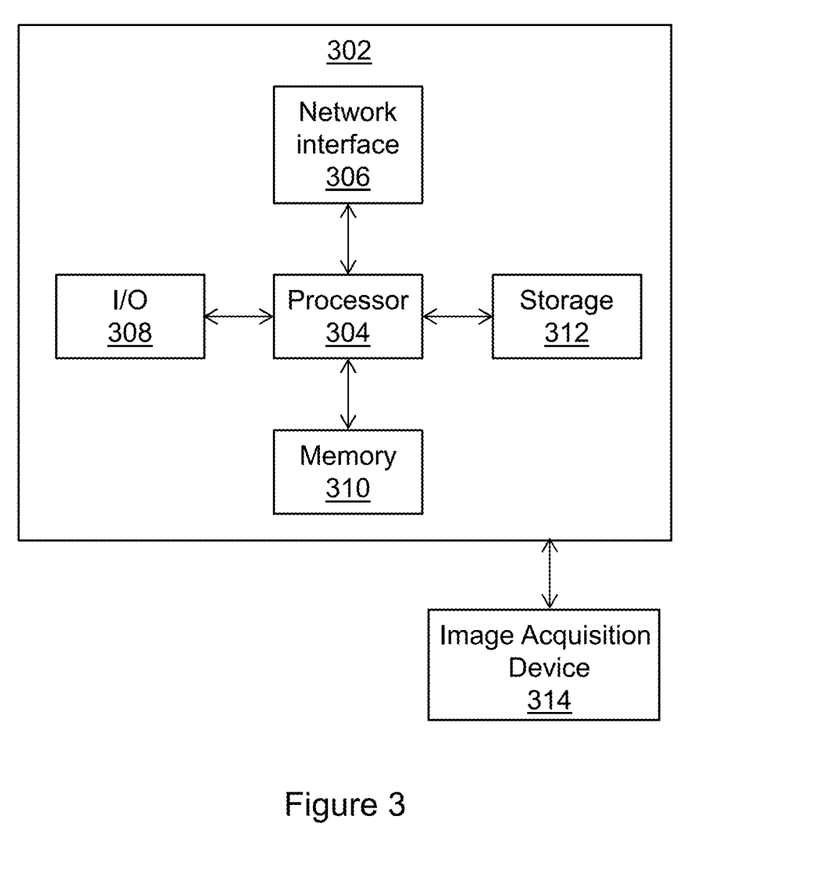
FIG. 3 shows a high-level block diagram of a computer that may be used to implement one or more embodiments.

A high-level block diagram of an example computer 302 that may be used to implement systems, apparatus, and methods described herein is depicted in FIG. 3. Computer 302 includes a processor 304 operatively coupled to a data storage device 312 and a memory 310. Processor 304 controls the overall operation of computer 302 by executing computer program instructions that define such operations. The computer program instructions may be stored in data storage device 312, or other computer readable medium, and loaded into memory 310 when execution of the computer program instructions is desired. Thus, the method and workflow steps or functions of FIG. 1 can be defined by the computer program instructions stored in memory 310 and/or data storage device 312 and controlled by processor 304 executing the computer program instructions. For example, the computer program instructions can be implemented as computer executable code programmed by one skilled in the art to perform the method and workflow steps or functions of FIG. 1. Accordingly, by executing the computer program instructions, the processor 304 executes the method and workflow steps or functions of FIG. 1. Computer 302 may also include one or more network interfaces 306 for communicating with other devices via a network. Computer 302 may also include one or more input/output devices 308 that enable user interaction with computer 302 (e.g., display, keyboard, mouse, speakers, buttons, etc.).

Processor 304 may include both general and special purpose microprocessors, and may be the sole processor or one of multiple processors of computer 302. Processor 304 may include one or more central processing units (CPUs), for example. Processor 304, data storage device 312, and/or memory 310 may include, be supplemented by, or incorporated in, one or more application-specific integrated circuits (ASICs) and/or one or more field programmable gate arrays (FPGAs).

Data storage device 312 and memory 310 each include a tangible non-transitory computer readable storage medium. Data storage device 312, and memory 310, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 308 may include peripherals, such as a printer, scanner, display screen, etc. For example, input/output devices 308 may include a display device such as a cathode ray tube (CRT) or liquid crystal display (LCD) monitor for displaying information to the user, a keyboard, and a pointing device such as a mouse or a trackball by which the user can provide input to computer 302.

An image acquisition device 314 can be connected to the computer 302 to input image data (e.g., medical images) to the computer 302. It is possible to implement the image acquisition device 314 and the computer 302 as one device. It is also possible that the image acquisition device 314 and the computer 302 communicate wirelessly through a network. In a possible embodiment, the computer 302 can be located remotely with respect to the image acquisition device 314.

Any or all of the systems and apparatus discussed herein may be implemented using one or more computers such as computer 302.

One skilled in the art will recognize that an implementation of an actual computer or computer system may have other structures and may contain other components as well, and that FIG. 3 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   receiving one or more 3D (three dimensional) medical images of one or more anatomical objects of a patient;
   determining correspondences between 2D (two dimensional) slices of the one or more 3D medical images and points on a 2D map representing the one or more anatomical objects by:
      annotating an atlas of the one or more anatomical objects with anatomical features that correspond to anatomical features in the 2D map,
      segmenting anatomical structures, using a trained machine learning based segmentation network, from 1) the one or more 3D medical images and 2) the annotated atlas, and
      registering the annotated atlas with the one or more 3D medical images to establish the correspondences between the 2D slices of the one or more 3D medical images and the points on the 2D map based on the anatomical structures segmented from the one or more 3D medical images and the anatomical structures segmented from the annotated atlas;
   updating the 2D map with patient information extracted from the one or more 3D medical images;
   presenting the updated 2D map with the determined correspondences to a user via a display device;
   receiving user input, from the user interacting with the display device, selecting one or more of the points on the updated 2D map; and
   in response to receiving the user input, displaying, to the user via the display device, one or more of the 2D slices that correspond to the selected one or more points based on the determined correspondences.

2. The method of claim 1, wherein determining correspondences between 2D (two dimensional) slices of the one or more 3D medical images and points on a 2D map representing the one or more anatomical objects comprises:
   determining correspondences between locations in the one or more 3D medical images and the points on the 2D map.

3. The method of claim 1, wherein determining correspondences between 2D (two dimensional) slices of the one or more 3D medical images and points on a 2D map representing the one or more anatomical objects comprises:
   creating the atlas of the one or more anatomical objects.

4. The method of claim 1, wherein the one or more anatomical objects is associated with a rotator cuff of the patient and the 2D map comprises a 2D representation of one or more muscles of the rotator cuff coupled between a humerus bone and a scapula bone.

5. The method of claim 1, wherein the one or more anatomical objects is associated with a rotator cuff of the patient and updating the 2D map with patient information extracted from the one or more 3D medical images comprises:
   automatically determining a muscle quality of one or more muscles of the rotator cuff from the one or more 3D medical images using a trained machine learning based network; and
   representing the one or more muscles in the 2D map based on the automatically determined muscle quality.

6. The method of claim 1, wherein the one or more anatomical objects is associated with a rotator cuff of the patient and updating the 2D map with patient information extracted from the one or more 3D medical images comprises:
   automatically determining a location and a size of a tear in a muscle of the rotator cuff from the one or more 3D medical images using a trained machine learning based network; and
   representing the tear in the muscle in the 2D map based on the automatically determined location and size of the tear.

7. The method of claim 1, wherein the 2D map comprises text labels identifying structures of the one or more anatomical objects.

8. An apparatus comprising:
   means for receiving one or more 3D (three dimensional) medical images of one or more anatomical objects of a patient;
   means for determining correspondences between 2D (two dimensional) slices of the one or more 3D medical images and points on a 2D map representing the one or more anatomical objects by:
      means for annotating an atlas of the one or more anatomical objects with anatomical features that correspond to anatomical features in the 2D map, and
      means for registering the annotated atlas with the one or more 3D medical images to establish the correspondences;
   means for updating the 2D map with patient information extracted from the one or more 3D medical images;
   means for presenting the updated 2D map with the determined correspondences to a user via a display device;
   means for receiving user input, from the user interacting with the display device, selecting one or more of the points on the updated 2D map; and
   in response to receiving the user input, means for displaying, to the user via the display device, one or more of the 2D slices that correspond to the selected one or more points based on the determined correspondences.

9. The apparatus of claim 8, wherein the means for determining correspondences between 2D (two dimensional) slices of the one or more 3D medical images and points on a 2D map representing the one or more anatomical objects comprises:
   means for determining correspondences between locations in the one or more 3D medical images and the points on the 2D map.

10. A non-transitory computer readable medium storing computer program instructions, the computer program instructions when executed by a processor cause the processor to perform operations comprising:
   receiving one or more 3D (three dimensional) medical images of one or more anatomical objects of a patient;
   determining correspondences between 2D (two dimensional) slices of the one or more 3D medical images and points on a 2D map representing the one or more anatomical objects by:
      annotating an atlas of the one or more anatomical objects with anatomical features that correspond to anatomical features in the 2D map, and
      registering the annotated atlas with the one or more 3D medical images to establish the correspondences;
   updating the 2D map with patient information extracted from the one or more 3D medical images;
   presenting the updated 2D map with the determined correspondences to a user via a display device;

receiving user input, from the user interacting with the display device, selecting one or more of the points on the updated 2D map; and in response to receiving the user input, displaying, to the user via the display device, one or more of the 2D slices that correspond to the selected one or more points based on the determined correspondences.

11. The non-transitory computer readable medium of claim 10, wherein determining correspondences between 2D (two dimensional) slices of the one or more 3D medical images and points on a 2D map representing the one or more anatomical objects comprises:

creating the atlas of the one or more anatomical objects.

* * * * *